United States Patent
Breunig et al.

(10) Patent No.: US 9,885,052 B2
(45) Date of Patent: Feb. 6, 2018

(54) METHOD FOR THE ORAL/MUCOSAL VACCINATION BY MEANS OF RECOMBINANT YEASTS

(75) Inventors: Karin Breunig, Berlin (DE); Sven-Erik Behrens, Halle/Saale (DE)

(73) Assignee: Martin-Luther-Universitaet Halle-Wittenberg, Halle/Saale (DE)

( * ) Notice: Subject to any disclaimer, the term of this patent is extended or adjusted under 35 U.S.C. 154(b) by 615 days.

(21) Appl. No.: 13/129,267

(22) PCT Filed: Nov. 13, 2009

(86) PCT No.: PCT/DE2009/001623
§ 371 (c)(1),
(2), (4) Date: Aug. 6, 2011

(87) PCT Pub. No.: WO2010/054649
PCT Pub. Date: May 20, 2010

(65) Prior Publication Data
US 2011/0293659 A1    Dec. 1, 2011

(30) Foreign Application Priority Data
Nov. 14, 2008  (DE) .................. 10 2008 057 451

(51) Int. Cl.
| C12N 1/19 | (2006.01) |
| C12N 15/81 | (2006.01) |
| A61K 39/12 | (2006.01) |
| C07K 14/005 | (2006.01) |
| G01N 33/569 | (2006.01) |
| A61K 39/00 | (2006.01) |

(52) U.S. Cl.
CPC ............ *C12N 15/815* (2013.01); *A61K 39/12* (2013.01); *C07K 14/005* (2013.01); *G01N 33/56983* (2013.01); *A61K 39/00* (2013.01); *A61K 2039/523* (2013.01); *A61K 2039/542* (2013.01); *A61K 2039/552* (2013.01); *C12N 2770/24322* (2013.01); *C12N 2770/24334* (2013.01)

(58) Field of Classification Search
None
See application file for complete search history.

(56) References Cited

U.S. PATENT DOCUMENTS

| 5,541,102 A | * | 7/1996 | Donis et al. .................. 435/325 |
| 5,593,858 A | * | 1/1997 | Fleer et al. .................. 435/69.1 |
| 5,830,463 A | * | 11/1998 | Duke et al. ................ 424/93.51 |
| 7,083,787 B2 | * | 8/2006 | Duke et al. ................ 424/184.1 |

FOREIGN PATENT DOCUMENTS

| EP | 1 790 332 | 5/2007 |
| WO | WO-99/15900 | 4/1999 |

OTHER PUBLICATIONS

Franzusoff et al. Yeasts encoding tumour antigens in cancer immunotherapy. Expert Opin Biol Ther. Apr. 2005;5(4):565-75.*

(Continued)

*Primary Examiner* — Michelle S Horning
(74) *Attorney, Agent, or Firm* — Norris McLaughlin & Marcus P.A.

(57) ABSTRACT

Recombinant yeast cells are produced which are used for vaccination, among other uses for the oral vaccination by feeding.

21 Claims, 2 Drawing Sheets

(56) References Cited

OTHER PUBLICATIONS

The Dictionary of Immunology. 1995, fourth edition by Academic Press Limited, definition for "vaccination".*
Cohen. Science. Jul. 1, 2005;309(5731):99. Is an effective HIV vaccine feasible?*
Srivastava et al. Neutralizing antibody responses to HIV: role in protective immunity and challenges for vaccine design. Expert Rev Vaccines. Aug. 2004;3(4 Suppl):S33-52. Review.*
Schweitzer et al. Overview of the Flaviviridae With an Emphasison the Japanese Encephalitis Group Viruses. Labmedicine, vol. 40, No. 8, 2009, pp. 493-499.*
Rollier et al. Control of Heterologous Hepatitis C Virus Infection in Chimpanzees is Associated with the Quality of Vaccine-Induced Peripheral T-Helper Immune Response. J Virol. 2004, 78(1): 187-196.*
Shirai et al. An Epitope in Hepatitis C Virus Core Region Recognized by Cytotoxic T Cells in Mice and Humans. J Virol, 1994, 68(5): 3334-3342.*
Huang et al. Recent development o therapeutics for chronic HCV infection. Antiviral Res 71 (2006) 351-362.*
Tan et al. Strategies for hepatitis C therapeutic intervention: now and next. Curr Opin in Pharmacology, 2004, 4: 465-470.*
Racanelli et al. Presentation of HCV antigens to naive CD8+T cells: why the where, when, what and how are important for virus control and infection outcome. Clin Immunol. Jul. 2007;124(1):5-12.*
Koziel et al. Hepatitis C virus (HCV)-specific cytotoxic T lymphocytes recognize epitopes in the core and envelope proteins of HCV. J Virol. Dec. 1993;67(12):7522-32.*
Berzofsky et al. Progress on new vaccine strategies against chronic viral infections. J Clin Invest. Aug. 2004;114(4):450-62.*
Zenke et al. Gal80 proteins of Kluyveromyces lactis and *Saccharomyces cerevisiae* are highly conserved but contribute differently to glucose repression of the galactose regulon. Mol Cell Biol. Dec. 1993;13(12):7566-76.*

* cited by examiner

METHOD FOR THE ORAL/MUCOSAL VACCINATION BY MEANS OF RECOMBINANT YEASTS

BACKGROUND OF THE INVENTION

Controlling infectious diseases is still one of the greatest challenges in both human and veterinary medicine. The situation is particularly complex in the case of viral infections, which, in contrast to bacterial infections, generally cannot be treated with broad-spectrum active substances and are the cause of major economic damages. Developing novel, effective vaccination strategies against viral illnesses is therefore extremely important.

"Attenuated" viruses, i.e. viruses modified by mutagenesis that have significantly reduced or no virulence ("live vaccines") or inactivated viruses ("dead vaccines") are traditionally used for prophylactic and also for therapeutic vaccination against viral diseases. Recently so-called "subunit vaccines" or "subunit marker vaccines" have become more established, wherein defined genetically produced "major antigens" of the pathogen are used for vaccination. The term "marker vaccine" implies that vaccinated individuals may be clearly differentiated from naturally infected individuals using subsequent diagnostic analysis. Major antigens are for instance proteins of the virus shell or virus capsid that may induce a humoral and/or cellular immune response in the host in the absence of a complete virus particle, and as a result of this viral infection may be preventively or therapeutically defended or combated. A "subunit vaccination" requires that major antigens are characterized. Production (expression) and immunogenic formulation of such proteins ("antigen formulation") become key for the vaccination process, especially since virus shell proteins are generally not water-soluble and may only rarely be produced recombinantly in bacterial expression systems. Methods for obtaining "subunit" vaccines in a purified form and for assuring their storability are correspondingly complex.

SUMMARY OF THE INVENTION

Yeasts for expression systems for recombinant proteins combine the economic advantages of bacterial systems with the organizational form typical of higher cells. They are compartmented by intracellular membrane systems, which fundamentally distinguishes them from bacterial host systems and enables the expression of membrane-anchored viral shell proteins or even entire virus capsids. In addition, the beta-glucanes, glucose polymers from which the yeast cell wall is constructed, have an immune-stimulating effect that has been known for some time. It was therefore the object to develop a method in which complete yeasts may be employed for vaccination. The object was attained in that by means of genetic methods genes for immunogenic determinants are planted into the genome of non-pathogenic yeasts and expressed and these recombinant yeast cells are employed directly for vaccination, inter alia for oral vaccination by feeding.

*Kluyveromyces lactis*

*Kluyveromyces lactis* belongs to the so-called food grade yeasts with GRAS status (generally regarded as safe). Like baker's yeast, which has been tested and proven as a food additive over centuries, the *K. lactis* yeast, which is frequently used in dairy products, is also considered safe in the food industry.

Oral/Mucosal Vaccination

The following options are available for administering vaccines/antigens: subcutaneous, intramuscular, parenteral or mucosal/oral options. While in the first three cases cited the antigens travel directly into the blood or lymphatic system, with mucosal/oral application the exposition of the antigen occurs via mucosa of the bronchial or gastrointestinal tract. The term mucosal/oral thus includes both nasal/bronchial administration and oral administration of antigens. Both bronchial and intestinal mucosa are permanently exposed to pathogens and represent per se a significant barrier to absorption of infectious agents. In the human body, the immune system associated with mucosal surfaces, especially that of the mucosal intestinal epithelium, includes e.g. approx. 90% of all immunocompetent cells. The antigen is absorbed and presented by the dendritic cells and M cells of the "Peyer's patches" (known collectively as MALT, mucosa-associated lymphoid tissue) in the intestinal mucosa, in the so-called inductive sites, but also by enterocytes and intestinal epithelium cells according to recent findings. The situation with the nasal/bronchial mucosa (BALT, bronchial associated lymphoid tissue) is analogous. After the immune response subsides, specific memory immune cells that as a rule provide long-lasting protection against the original antigen/pathogen occur in the entire organism, but also in the so-called effector sites of the mucosa.

Advantages of Oral/Mucosal Vaccination Methods.

Compared to parenteral immunization, oral/mucosal immunization requires the use of significantly higher quantities of antigens. In contrast to parenteral immunization, however, with oral/mucosal vaccination it is possible to induce a local immune response at the effector sites of the mucosa in addition to the systemic immune response. Especially with pathogens (such as e.g. bovine viral diarrhea virus, BVDV, and classical swine fever virus, CSFV; also see below), which also are transmitted via mucosa, a mucosal/oral vaccination has the potential to produce active and long-lasting immunity. Additional major advantages of oral vaccination are good acceptance and economy. In the most favorable case the vaccines may be produced at low cost and may be uncomplicated to administer with food. Moreover, vaccines of the invention having long storability outside a cold train can be produced according to the invention.

Mucosal/oral administration of yeast strains that express virus antigens is therefore not only safe but might also have additional health-promoting and adjuvant effects.

Again, the object was to develop an expression system based on *Kluyveromyces lactis*, which system permits the deliberate integration of foreign genes in the yeast genome and thus permits corresponding antigen formulations. An additional object was to employ a recombinant *K. lactis* strain that expresses a specific virus antigen for a vaccination, inter alia for a mucosal/oral vaccination.

DETAILED DESCRIPTION OF THE INVENTION

In accordance with the invention, a *K. lactis* strain, preferably VAK367-D4 and variants of this strain, was generated using genetic methods and permits the deliberate integration of foreign genes on the LAC4 locus of the yeast genome without it being necessary to introduce additional DNA sequences (selection marker or the like). The recombinant yeast strains are stable without selection pressure and may be cultivated under fermentation conditions to create high densities. Foreign gene expression may be induced by metered lactose or galactose or, after turning off the KIGAL80 regulator gene, may be constitutively activated. Foreign gene expression may be quantified indirectly using expression of an endogenous reporter gene.

A series of recombinant variants building on the *K. lactis* VAK367-D4 strain was generated. In general these variants express inducibly significant quantities of a protein, or domains of this protein, or domains of this protein fused with heterogenous protein domains. The related heterogenous protein domains act to deliberately stimulate the immune response (adjuvant purposes) and to deliberately compartmentalize the expressed foreign protein in the yeast cell. In addition to adjuvant effects, compartmentalization of the expressed foreign protein is important for optimizing expression and for formulating the expression product. One of these recombinant *K. lactis* strains was successfully employed for mucosal/oral vaccination (see exemplary embodiments).

Exemplary Embodiments

1. Production of the *K. lactis* VAK367-D4 Strain (Met' ura3 lac4::ScURA3).

Figure 1:
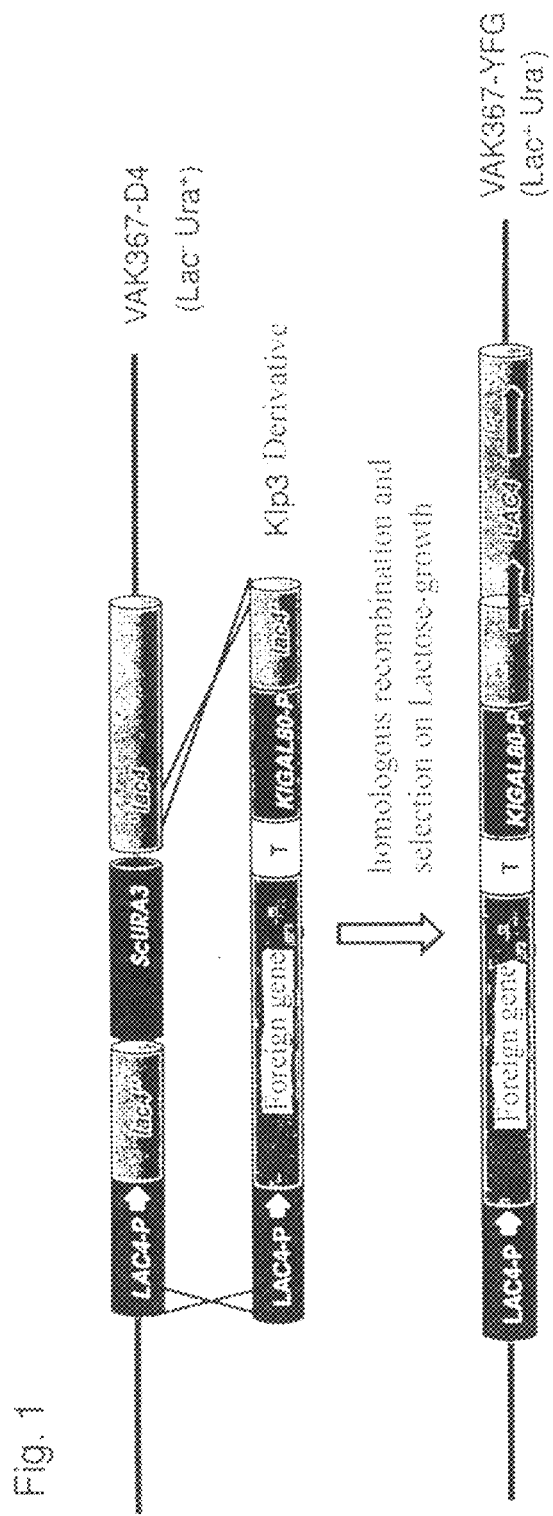
FIG. 1 is a schematic illustration relating to exemplary embodiment 1.

The initial VAK367 strain for heterologous expression of foreign proteins has the following properties: It permits cultivation to produce high cell density without intracellular proteins being detectably released. This strain is distinguished from many closely related *K. lactis* strains in this regard. The VAK367 strain was derived from two rounds of mutagenesis of the CBS 2359 strain (Central bureau voor Schimmelcultures, Fungal Biodiversity Centre) and is auxotrophic for the amino acid methionine and the nucleobase uracil. Using genetic methods, the VAK367-D4 strain was derived from the VAK367 strain (deposited with the Deutsche Sammlung von Mikroorganismen und Zellkulturen GmbH (DSMZ) in Braunschweig) in that the sequence of +358 to +1181 of the LAC4 gene was replaced with the ScURA3 gene using the plasmid pD4-2. The VAK367-D4 strain now permits the integration of foreign genes at the LAC4 locus without additional markers in that lactose growth is selected. When using a suitable integration vector such as e.g. Klp3 (see below) by homologous recombination, the disruption cassette is replaced such that an intact LAC4 gene is reconstituted and the ScURA3 marker is lost. (FIG. 1)

2. Production of an Integration Vector that Permits the Inducible Expression of Foreign genes.

Vector: Klp3

The Klp3 vector is an *E. coli* vector based on YRp7 that cannot replicate autonomously in yeasts because the ARS1 sequence was deleted. Klp3 includes *K. lactis* sequences that make it possible to integrate at the LAC4 locus using homologous recombination (upstream region of LAC4 and 5' end of the LAC4 reading frame). A DNA segment that includes the TEF1 terminator and the KIGAL80 promotor was inserted between the LAC4 promotor and the transcription start. Thus the LAC4 reading frame is under control of the KIGAL80 promotor that is co-regulated via the KIGal4 transcription factor with the LAC4 promotor (Zenke et al. 1993, Molecular and Cellular Biology, 13:7566-7576). This design makes it possible to track induction of foreign gene expression by measuring the LAC4-coded β-galactosidase. Klp3 permits the integration of the foreign gene between LAC4 promotor and TEF1 terminator via the unical SalI interface. For integrating the expression cassette, Klp3 is digested with HpaI or EcoRI and transformed into *K. lactis* VAK367-D4. In doing so the expression cassette is separated form the *E. coli* vector portion so that the resulting strains do not contain any bacterial sequences.

Figure 2:
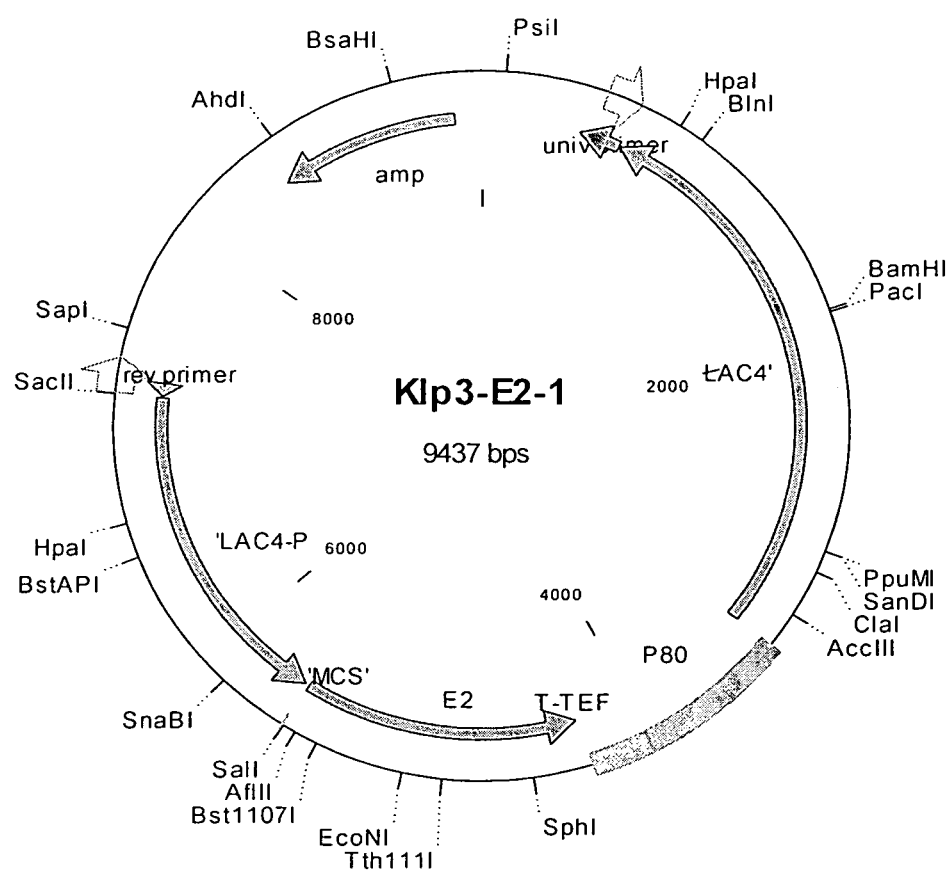
FIG. 2 is a schematic illustration relating to exemplary embodiment 2.

Plasmid Klp3-E2-1 (9437 bp) (FIG. 2)

The gene segment of the BVDV virus that codes for the viral structure protein E2 was inserted into the Sal interface between LAC4 promotor and TEF1 terminator as SalI-XhoI fragment. The KIGAL80 promotor is downstream and was fused to the 5' end of the LAC4 ORF.

The plasmid was cut with HPaI and the larger HpaI fragment was integrated with the E2-ORF chromosomally using homologous recombination. The lac4::URA3 gene locus was replaced and the intact LAC4 gene was reconstituted. Growth on lactose medium was used for selection. The loss of the URA3 gene was confirmed by the uracil auxotrophy. The sequence for the corresponding gene locus was confirmed using DNA sequencing. (Sequence log 1)

3. Formulation of the E2 Major Antigens of BVDV and CSFV.

A major antigen is characterized by BVDV (bovine viral diarrhea virus), the pathogen of bovine viral diarrhea and mucosal disease (BVD/MD), and also by CSFV (classical swine fever virus), the pathogen of classical swine fever (CSF). This is the "envelope" (virus-shell integrated) protein E2. Even in the absence of a virus particle, E2 induces a massive humoral immune response, i.e. the formation of effectively virus-neutralizing antibodies. Genetically formulating E2 made it possible to further strengthen the immunogenic potential of the protein and also to produce a cellular immune response. The specific and exclusive immune response to individual protein domains of E2, some of which were genetically formulated, made it possible to discriminate between vaccinated animals and animals infected with the field virus, e.g. by means of the ELISA method.

4. Design of a *K. lactis* Strain that Expresses the BVDV E2 Protein VAK367-E2-1, a *K. lactis* strain, was produced by means of the inventive technology. In this strain, a segment of the BVDV genome (CP7 strain) was integrated into the yeast genome. The corresponding BVDV gene segment included the area that included protein for the E2 and parts of the adjacent E1 and p7-coding regions of the BVDV genome. The E1 and p7 regions include the signal sequences needed for correctly processing the E2 protein (sequence log 2). Correct processing (maturation) of the BVDV E2 protein occurs via signalases.

Expression of E2 in cells of the VAK367-E2-1 *K. lactis* strain may be established by means of a specifically developed immunofluorescence detection method. An ELISA method specially developed for detecting the BVDV E2 permits detection and quantification of the heterologously expressed antigen. It was possible to use the analog ELISA method for precisely quantifying the antibody titer of immunized animals. Virus neutralization methods and methods for characterizing antibodies and T cells were employed as routine methods.

A novel qRT-PCR method makes it possible to detect and quantify BVDV RNA genomes from serum and cell culture supernatants.

5. Demonstrating the Effectiveness of *K. lactis* Strain VAK367-E2-1 in Mucosal/Oral Immunization Studies Study 1

In animal testing an emulsion of naive *K. lactis* was applied to a significant number of mice under standard conditions. Various immunization schemes were used.

The main criteria were different quantities of supplied yeasts (3—max. 8% portion of daily food intake) and different "booster intervals."

Results:
(i) General tolerance for *K. lactis* was demonstrated: oral administration of the yeast emulsions did not cause any visible changes in the findings for the animals.
(ii) Administration of *K. lactis* led to a clearly detectable humoral immune response to certain yeast proteins. Using the western blot method it was possible to establish a significant and specific antibody response to yeast proteins in the animals that had been fed with *K. lactis* compared to control animals. Yeast proteins thus have an immunogenic effect per se. In addition to the proof of principle that an immune response may be produced with the oral application of *K. lactis*, it was indicated that the oral administration of yeasts in combination with a recombinant antigen may attain an additional adjuvant effect.

Study 2

In other animal studies that used a significant number of mice, oral vaccinations were administered with an optimized immunization scheme (see Study 1) and with recombinant *K. lactis* of the VAK367-E2-1 strain.

Results:
(i) Using the special ELISA method it was possible to detect the formation of anti-BVDV E2 antibodies in the mice vaccinated with *K. lactis* strain VAK367-E2-1 compared to control mice (immunized with naïve *K. lactis*).
(ii) In a neutralization test with BVDV on bovine culture cells it was possible to detect a neutralizing effect of anti-sera from mice that had been immunized with *K. lactis* of the VAK367-E2-1 strain, again in comparison to the sera from control mice.
(iii) The immune response could be increased by using adjuvants such as CpG-ODN and QuilA.
(iv) It was possible to attain effective protection using mucosal/oral immunization with the recombinant *K. lactis* VAK367-E2-1 strain. This could be demonstrated in challenge experiments with recombinant vaccine viruses that express the BVDV E2 protein.

The results of the study prove that in accordance with the invention foreign genes without additional selection markers may be deliberately integrated into them by means of producing a *K. lactis* strain and variants of this strain. The resulting recombinant descendants of the *K. lactis* strains in question may be used for expression purposes for the subsequent biochemical representation of a heterologous protein. The cells of the corresponding recombinant *K. lactis* strains may be employed directly for mucosal/oral or parenteral immunization.

The invention claimed is:

1. A method of vaccination, comprising oral/mucosal administration of a vaccine comprising a recombinant yeast, wherein said recombinant yeast comprises a genomically integrated expression cassette comprising lactose inducible LAC4 promoter from *Kluyveromyces lactis*, a foreign gene or a part of a foreign gene expressing an immunogenic protein, a transcription terminator and GAL80 promoter from *K. lactis* (KIGAL80-P) which drives transcription of a LAC4 coding sequence, wherein the foreign gene or the part of the foreign gene is flanked by the lactose inducible LAC4 promoter and the transcription terminator, which transcription terminator is followed downstream by the KIGAL80-P.

2. The method in accordance with claim 1, wherein the recombinant yeast is *Kluyveromyces lactis*.

3. The method in accordance with claim 1, in which said recombinant yeast is employed as an expression system.

4. The method in accordance with claim 3, wherein the recombinant yeast allows lactose-inducible expression of the foreign gene or said part of a foreign gene.

5. The method in accordance with claim 1, wherein said recombinant yeast is characterized by absence of any foreign selection markers apart from the foreign gene or said part of a foreign gene.

6. The method in accordance with claim 1, further comprising quantification of the expression of the foreign gene or said part of a foreign gene by expression of an endogenous reporter gene that is a co-regulated *Kluyveromyces lactis*-intrinsic beta-galactosidase gene (LAC4).

7. The method in accordance with claim 1, wherein the foreign gene or said part of a foreign gene expresses a structure protein from the bovine viral diarrhea virus (BVDV).

8. The method in accordance with claim 1, wherein the vaccine has long storability outside of a cold environment.

9. The method in accordance with claim 1, wherein the recombinant yeast of the vaccine comprises complete yeast cells which provide a specific immunization against the expressed foreign protein or expressed foreign protein part.

10. A method of vaccination comprising inhaled, bronchial, oral or nasal administration of a vaccine, comprising a recombinant yeast comprising complete yeast cells which provide a specific immunization against expressed foreign protein, wherein the recombinant yeast comprises a genomically integrated expression cassette comprising the lactose inducible LAC4 promoter from *Kluyveromyces lactis*, a foreign gene or a part of a foreign gene expressing an immunogenic protein, a transcription terminator and GAL80 promoter from *K. lactis* (KIGAL80-P) which drives transcription of a LAC4 coding sequence, wherein the foreign gene or the part of the foreign gene is flanked by the lactose inducible LAC4 promoter and the transcription terminator, which transcription terminator is followed downstream by the KIGAL80-P.

11. The method in accordance with claim 1 or 10, further comprising subsequently detecting neutralizing antibodies in sera from individuals who were immunized by said vaccine.

12. The method in accordance with claim 1 or 10, further comprising subsequently detecting neutralizing antibodies against a BVDV E2 protein in sera from individuals who were immunized by said vaccine.

13. The method in accordance with claim 1 or 10, further comprising detecting immunization using a challenge with antigen in individuals who were immunized by said vaccine.

14. The method in accordance with claim 13, wherein the antigen is a viral antigen.

15. The method in accordance with claim 14, wherein the viral antigen is BVDV E2.

16. A method of vaccination comprising oral/mucosal administration of a vaccine comprising a recombinant yeast derived from the strain *Kluyveromyces lactis* VAK367-D4 by homologous recombination resulting in replacement of the genomic lac4::URA3 locus with an expression cassette comprising a foreign gene or a part of a foreign gene expressing an immunogenic protein, lactose inducible LAC4 promoter from said strain, a transcription terminator, and GAL80 promoter from *K. lactis* (KlGAL80-P) which drives transcription of a LAC4 coding sequence, wherein the foreign gene or the part of the foreign gene is flanked by the lactose inducible LAC4 promoter and the transcription terminator, which transcription terminator is followed downstream by the KlGAL80-P.

17. The method of vaccination of claim 1, wherein the vaccine comprises a recombinant yeast of the strain *Kluyveromyces lactis* in which a foreign gene segment of Bovine Viral Diarrhea Virus coding for viral structure protein E2 is inserted into a gene of the strain, whereby, upon oral or mucosal administration of the vaccine to an animal, an immune response to Bovine Viral Diarrhea Virus is induced in the animal.

18. The method in accordance with claim 1, wherein the foreign gene or part of a foreign gene is deliberately integrated into the yeast genome without introduction of an additional marker.

19. The method of claim 1, 10, 16, or 18, wherein said recombinant yeast is characterized by high genetic stability of the expression cassette even during growth of said recombinant yeast under non-selective conditions due to absence of any extended DNA-sequence repeats in the expression cassette.

20. The recombinant yeast as recited in claim 1.

21. The vaccine as recited in claim 1.

* * * * *